United States Patent
Jimenez et al.

(10) Patent No.: US 7,600,285 B2
(45) Date of Patent: Oct. 13, 2009

(54) ORAL CARE IMPLEMENT AND METHOD OF DECORATING

(75) Inventors: Eduardo Jimenez, Manalapan, NJ (US); Alberto Mantilla, Rego Park, NY (US); Tony Baxter, Hoboken, NJ (US); Diana Sierra, Fairview, NJ (US)

(73) Assignee: Colgate-Palmolive Company, New York, NY (US)

( * ) Notice: Subject to any disclaimer, the term of this patent is extended or adjusted under 35 U.S.C. 154(b) by 647 days.

(21) Appl. No.: 11/104,158

(22) Filed: Apr. 12, 2005

(65) Prior Publication Data

US 2006/0225231 A1    Oct. 12, 2006

(51) Int. Cl.
  *A46B 5/00* (2006.01)
  *A46B 17/00* (2006.01)
  *B25G 1/00* (2006.01)
(52) U.S. Cl. .......................... 15/22.1; 15/28; 15/143.1; 15/246; 16/110.1; 16/421; 16/436; 40/314
(58) Field of Classification Search ................. 15/22.1, 15/28, 143.1, 246; 16/110.1, 421, 430, 436; 40/314
See application file for complete search history.

(56) References Cited

U.S. PATENT DOCUMENTS

| | | | |
|---|---|---|---|
| 184,918 A | 11/1876 | Siddall | |
| 604,706 A | 5/1898 | Wiens et al | |
| 695,197 A | 3/1902 | Dillingham | |
| 1,133,622 A | 3/1915 | Darling | |
| 1,632,227 A | 6/1927 | Halsey | |
| 1,650,200 A | 11/1927 | Dougan | |
| 1,690,311 A | 11/1928 | Reich | |
| 1,811,660 A * | 6/1931 | Bausher | 40/314 |
| 1,899,242 A | 2/1933 | McNab | |
| 2,134,863 A | 11/1938 | Dvorak | |
| 2,173,451 A | 9/1939 | Lorber | |
| 2,179,266 A | 11/1939 | Lukenbilll | |
| D157,669 S | 3/1950 | Graves, Jr. | |
| 2,520,808 A | 8/1950 | Miller | |
| D176,578 S | 1/1956 | Kraver | |
| D190,382 S | 5/1961 | Harwood et al | |
| D201,237 S | 5/1965 | Corlin | |
| 3,189,069 A * | 6/1965 | Stowell | 81/177.1 |
| D204,118 S | 3/1966 | Corlin | |
| D204,119 S | 3/1966 | Corlin | |
| D204,183 S | 3/1966 | Corlin | |
| 4,283,808 A | 8/1981 | Beebe | |
| 4,436,965 A * | 3/1984 | Morse | 379/447 |
| 4,509,228 A | 4/1985 | Landsberger | |
| 4,617,697 A | 10/1986 | David | |

(Continued)

FOREIGN PATENT DOCUMENTS

DE    3622596    *    1/1987

(Continued)

*Primary Examiner*—Mark Spisich
(74) *Attorney, Agent, or Firm*—Amy M. Fernandez

(57) ABSTRACT

An oral care implement comprises a head and a body provided with a three-dimensional surface feature on the body that is generally undecorated. A cover is applied to the body and includes a decoration that is associated with the three-dimensional surface feature, such that the body, with the cover applied, appears to have a decorated three-dimensional surface feature.

12 Claims, 4 Drawing Sheets

U.S. PATENT DOCUMENTS

| | | | |
|---|---|---|---|
| 4,890,355 A | 1/1990 | Schulten | |
| 4,951,533 A | 8/1990 | Hillinger | |
| 4,969,231 A * | 11/1990 | Mader et al. | 16/421 |
| 5,251,380 A | 10/1993 | Craig | |
| 5,334,431 A * | 8/1994 | Longtin | 428/41.8 |
| 5,348,360 A | 9/1994 | Mencarelli et al. | |
| D375,036 S | 10/1996 | David et al. | |
| 5,598,655 A * | 2/1997 | McGarrah | 40/606.02 |
| 5,623,739 A | 4/1997 | Thompson | |
| D381,206 S | 7/1997 | Mannino | |
| D383,307 S | 9/1997 | Klein et al. | |
| D388,680 S | 1/1998 | Lin | |
| 5,713,104 A | 2/1998 | Giampaolo, Jr. | |
| 5,729,864 A | 3/1998 | Lie et al. | |
| 5,848,453 A | 12/1998 | Racodon | |
| 5,860,190 A | 1/1999 | Cano | |
| 5,926,901 A | 7/1999 | Tseng et al. | |
| 6,006,396 A | 12/1999 | Hellinger et al. | |
| 6,006,403 A | 12/1999 | Battiato | |
| D420,222 S | 2/2000 | Angelini et al. | |
| D420,806 S | 2/2000 | Ayissi | |
| D426,958 S | 6/2000 | Moskovich et al. | |
| 6,108,870 A * | 8/2000 | Lo | 16/431 |
| D438,386 S | 3/2001 | Enriquez | |
| 6,202,242 B1 | 3/2001 | Salmon et al. | |
| D444,048 S | 6/2001 | Mangione | |
| 6,273,626 B1 | 8/2001 | Yazawa | |
| 6,367,113 B1 | 4/2002 | Usui | |
| D456,614 S | 5/2002 | Zemel | |
| 6,422,867 B2 | 7/2002 | Lang et al. | |
| D463,952 S | 10/2002 | Zemel | |
| 6,485,211 B1 | 11/2002 | Leo et al. | |
| D474,644 S | 5/2003 | Zemel | |
| 6,591,456 B2 | 7/2003 | DeLuca et al. | |
| 6,629,331 B2 | 10/2003 | Panfili et al. | |
| 6,709,185 B2 | 3/2004 | Lefevre | |
| 6,929,173 B2 * | 8/2005 | Toussant et al. | 232/38 |
| 2001/0002605 A1 | 6/2001 | Morawski et al. | |
| 2003/0000030 A1 | 1/2003 | Davies et al. | |
| 2003/0005549 A1 | 1/2003 | DeLuca et al. | |
| 2003/0028987 A1 | 2/2003 | Morawski et al. | |
| 2003/0066145 A1 * | 4/2003 | Prineppi | 15/22.1 |
| 2003/0123917 A1 | 7/2003 | Willat et al. | |
| 2003/0217434 A1 | 11/2003 | De Rosa | |
| 2004/0107523 A1 * | 6/2004 | Davies et al. | 15/143.1 |

FOREIGN PATENT DOCUMENTS

| | | | |
|---|---|---|---|
| GB | 2185209 | * | 7/1987 |
| GB | 2 345 019 | | 6/2000 |
| JP | 2001-186926 | * | 7/2001 |
| WO | WO 2004/039205 | | 5/2004 |

* cited by examiner

ORAL CARE IMPLEMENT AND METHOD OF DECORATING

FIELD OF THE INVENTION

This invention relates to an oral care implement and method of decorating the same, and more particularly to a method of applying a decorative cover to the body of an oral care implement such as a toothbrush handle.

BACKGROUND OF THE INVENTION

Kids' toothbrush handles are often fancifully decorated with colorful stickers having generic or licensed designs. Such designs are not only attractive and aesthetically pleasing, but usually drive the decision amongst a variety of brushes adorned with different designs.

It is known in the art to provide handle designs that are either two-dimensional or three-dimensional. The typical two-dimensional design is usually a decorative sticker or label of unlimited detail that is adhered or shrunk wrap to the handle and conforms to the shape of the handle. The production and application of the sticker adds an insignificant cost to the manufacture of the handle, as the sticker is manufactured separately and the application of such sticker usually requires a single manufacturing step. Such sticker or label provides a high level of flexibility for applying a complex decorative design to the handle of toothbrush. However, such decorative stickers or labels usually retain their two-dimensional character relative to a smooth, uncontoured or unsculpted handle.

Three-dimensional designs can take many forms. For example, some designs are molded and form part of the handle structure as shown in U.S. Pat. No. 6,202,242. In another example, an undecorated and uncontoured handle could be inserted into a preformed three-dimensional decorated sleeve as shown in U.S. Patent D426,958, which sleeve could be manufactured in a more efficient manner separately from the toothbrush and solely contributes to the three-dimensional character of the handle. In the molded example, and possibly also the sleeve example, multiple paint operations applied to the three-dimensional feature are usually required to deliver an aesthetically pleasing, colorful design. Each paint operation delivers a particular color to a particular area of the design, which requires a separate manufacturing step at an incremental added cost. The more paint operations, the greater the cost.

Manufacturers that use licensed designs must often comply with certain aesthetic requirements imposed by the licensor. Such requirements may require a certain level of detail that can only be accomplished with a certain number of paint operations, for example. However, if the number of paint operations makes the design too expensive to manufacture, then the licensee must negotiate the use of a simpler design to the potential commercial detriment of both the licensor and the manufacturer. There is a need, therefore, for a way to provide a three-dimensional design that is aesthetically intricate and economical to manufacture.

SUMMARY OF THE INVENTION

An oral care implement is provided with a head and a body. The body is further provided with a three-dimensional surface feature that is generally undecorated. A generally two-dimensional cover is applied to at least a portion of the body that includes a decoration that is associated with the three-dimensional surface feature, preferably such that the body appears to have a decorated three-dimensional surface feature. A kit is disclosed that includes an oral care implement and a plurality of decorative covers to be applied to the oral care implement.

DETAILED DESCRIPTION OF THE PREFERRED EMBODIMENTS

Figure 1:
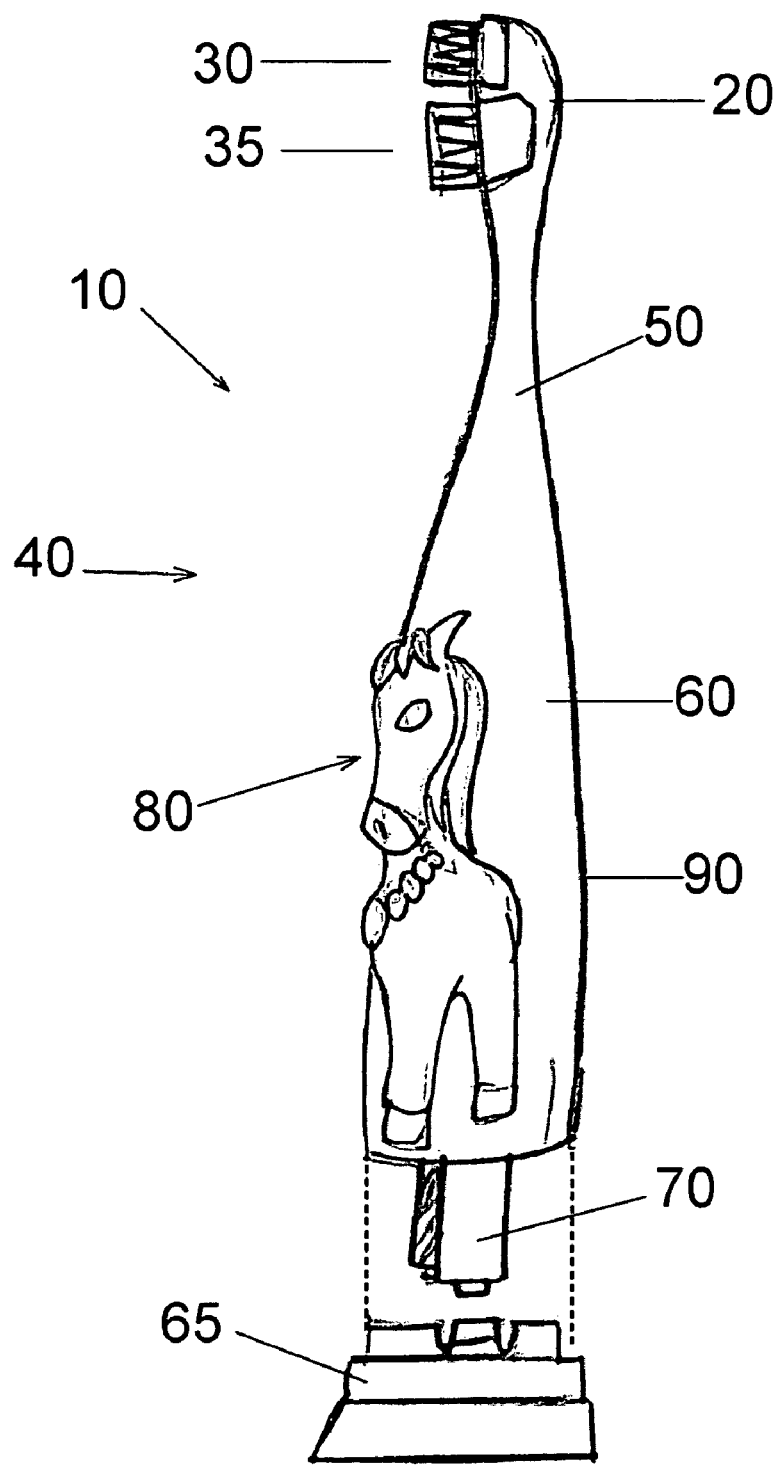
FIG. 1 illustrates one embodiment of an oral care implement in accordance with the invention.

The following detailed description is of the best mode or modes of the invention presently contemplated. Such description is not intended to be understood in a limiting sense, but to be an example of the invention presented solely for illustration thereof, and by reference to which in connection with the following description and the accompanying drawings one skilled in the art may be advised of the advantages and construction of the invention. In the various views of the drawings, like reference characters designate like or similar parts.

FIG. 1 illustrates one embodiment of an oral care implement 10, which will be illustrated and described herein for purposes of convenience as a toothbrush 10. Of course, other oral care implements, such as flossers, etc., are contemplated. In addition, while the present invention focuses on oral care implements, it will be understood that the inventive concept could be applied to other products, such as personal care products (e.g., razors, hair dryers, etc.), home care products (e.g. soap dispensers) and the like.

Toothbrush 10 generally comprises a head 20 with cleaning elements 30, 35 and a body 40 defined by a neck 50 and a handle 60. Toothbrush 10 of the current embodiment is illustrated as a powered toothbrush with a power element 70 included within the body 40 that drives one or both of the cleaning elements 30, 35 in a moving, rotational, dual-oscillating or counter-oscillating manner. Other ways of powering the cleaning elements 30, 35 are contemplated. Power element 70 could also energize other powered devices such as a light, sound generator or the like (not shown). However, it will be understood that the present invention is also applicable to a non-powered implement or toothbrush as well, and the discussion or illustration of a powered implement is not meant to be limiting.

A three-dimensional surface feature or design 80 is provided on the body 40, and more particularly the handle 60 in the illustrated embodiment, and is formed from a plurality of discontinuous surface contours that form a three-dimensional image. In the illustrated embodiment, the discontinuous surface contours include, but are not limited to, the arms, hands, face, legs, etc. of the cartoon character. The surface feature 80 could also be provided on the neck 50 portion exclusively or in addition to the handle 60. Surface feature 80 is generally integrally molded as part of the handle 60 in one manufacturing step, although it could be formed on the handle 60 after the handle shape is formed. In addition to the three-dimensional surface feature 80, the handle 60 includes at least one surface 90 that is not raised or three-dimensional and that is usually located on the rear of the handle 60.

Figure 2:
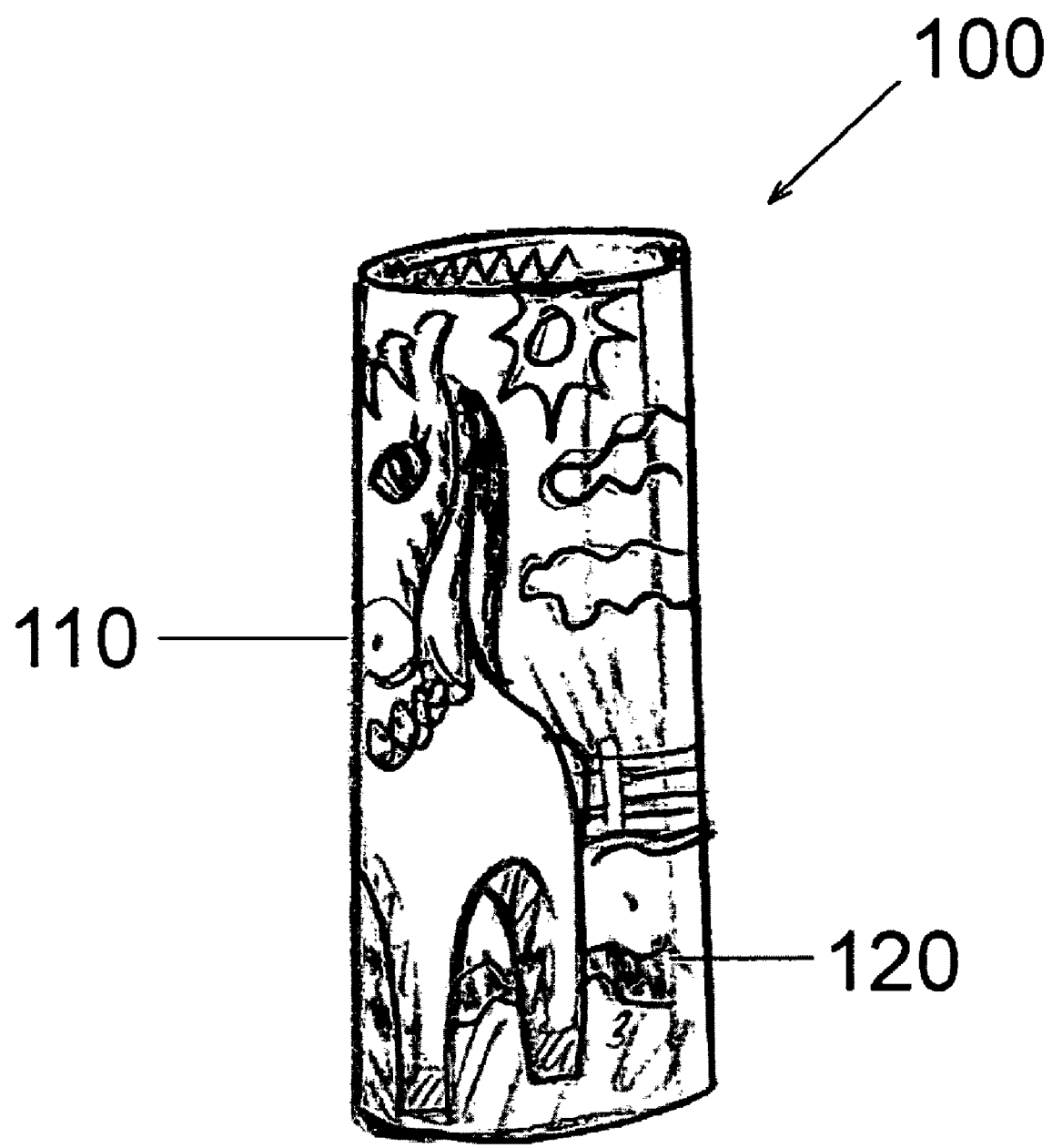
FIG. 2 illustrates a cover to be applied to the implement of FIG. 1.

The three-dimensional surface feature 80 is decorated through the application of a preferably two-dimensional cover 100 (FIG. 2) applied to at least a portion of the body 40.

Figure 3:
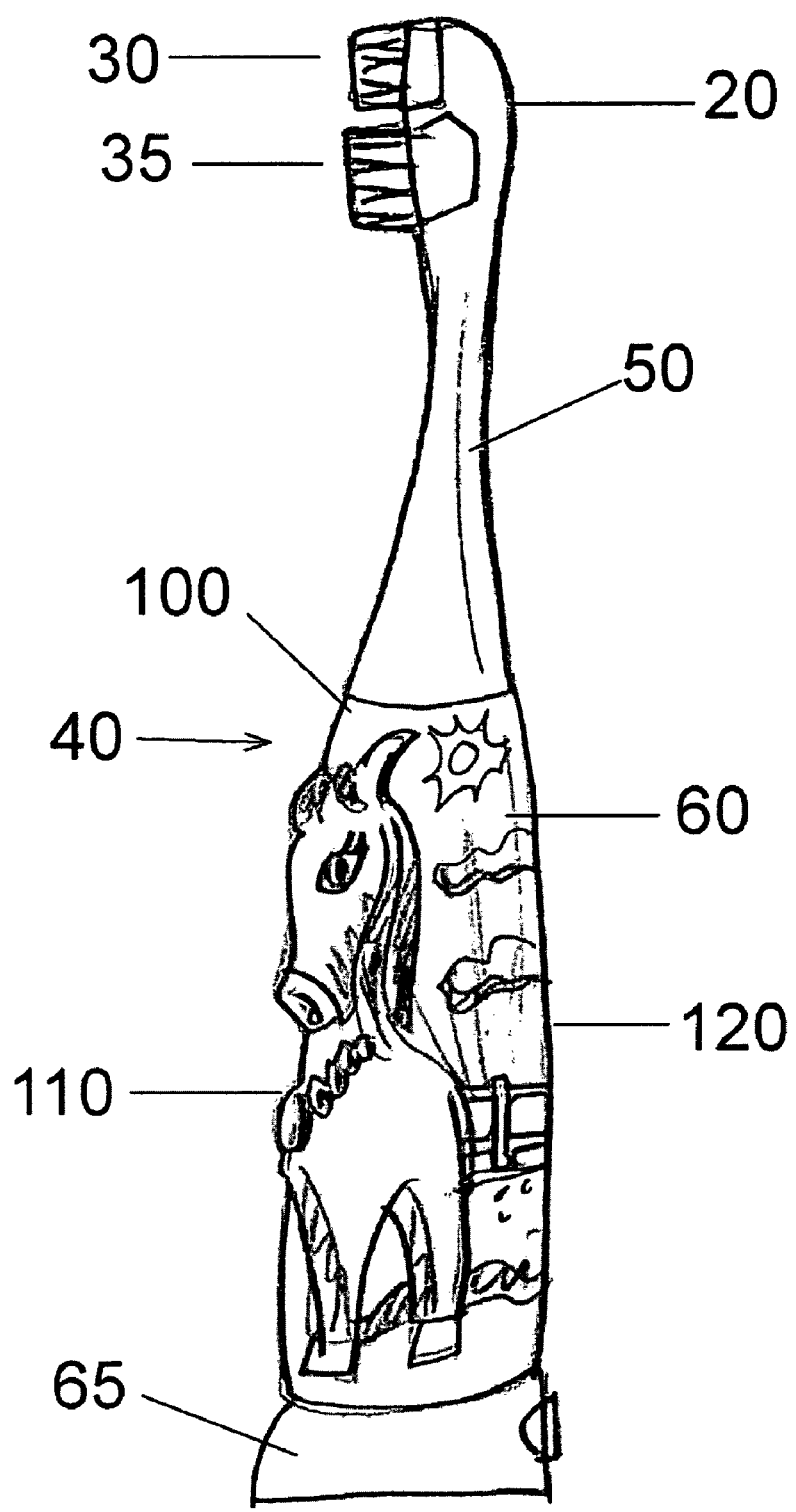
FIG. 3 illustrates the cover of FIG. 2 applied to the implement of FIG. 1.

Cover 100 is provided with a decoration 110 that is complimentary, or matches the three-dimensional surface feature provided on the handle 60, such that when the cover 100 is applied to the handle 60 as shown in FIG. 3, the three-dimensional surface feature appears to be decorated by the decoration 110. In other words, the three-dimensional surface feature 80 transforms the two-dimensional decoration 110 into a three-dimensional decoration. Of course, the cover 100 preferably also includes other decoration 120 that is applied over the surface 90 that is not raised or three-dimensional, thus completing the decoration of the entire handle if desired.

The cover 100 is preferably removably or non-adhesively applied to the handle 60, by a shrink fit, cling fit or the like, and is preferably formed from a relatively thin film of plastic. Of course, other cover materials are contemplated. A cover 100 in the nature of a static cling decal, provides the user with the option to apply the cover 100 to a completely different article, such as a mirror or window for example, and/or to be used as a decoration on other than the toothbrush 10. Alternatively, the cover is slideably attached to and optionally retained on the handle by an end cap 65 or the like. In these situations, removal and replacement or an alternative use of the cover as desired by the user becomes possible. In one alternative embodiment, the cover 100 is adhesively applied to the handle 60 during manufacture.

Figure 4:
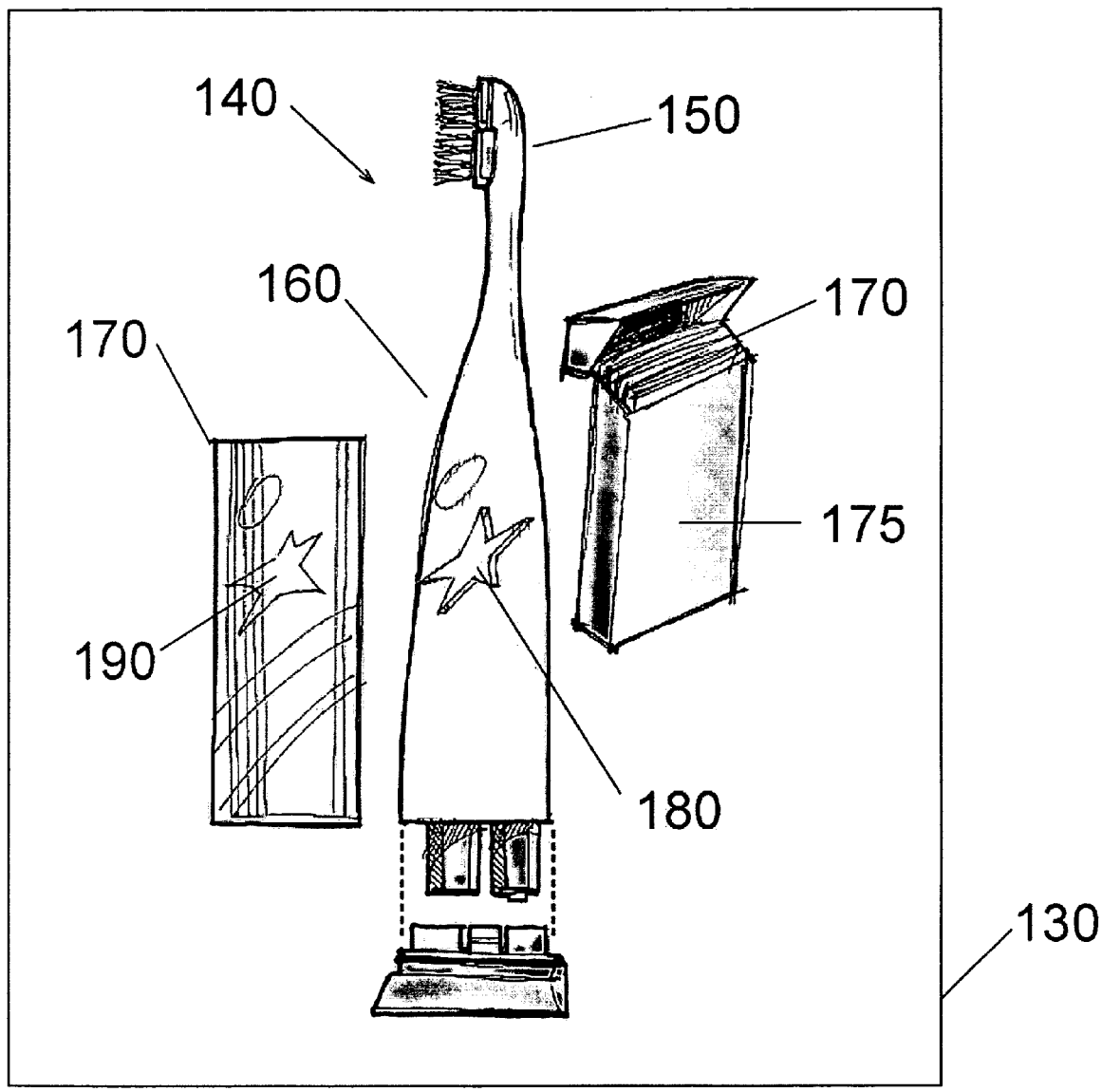
FIG. 4 illustrates one embodiment of a kit in accordance with the invention.

FIG. 4 illustrates a kit 130 comprising a toothbrush 140 having a head 150 and a body 160, and a plurality of covers 170 retained in a storage receptacle 175. In this embodiment, a three-dimensional surface feature 180 in the shape of a star is provided on the body 160, with a complimentary decoration 190 provided on the cover 170. The toothbrush 140 may be initially provided in the kit 130 without a cover 170, wherein each cover 170 in the storage receptacle 175 has a different design that compliments the three-dimensional surface feature 180. Alternatively, the toothbrush 140 may be vended with a cover 170 already applied. Either way, the kit enables the user to vary the handle design as desired.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention. Furthermore, the foregoing describes the invention in terms of embodiments foreseen by the inventor for which an enabling description was available, notwithstanding that insubstantial modifications of the invention, not presently foreseen, may nonetheless represent equivalents thereto.

What is claimed is:

1. An oral care implement comprising:
   a) a head,
   b) a body attached to the head and provided with a three-dimensional surface feature having three-dimensional surface contours,
   c) a cover applied to at least a portion of the body, the cover covering at least a portion of the three-dimensional surface feature and including a decoration that is associated with the three-dimensional surface feature and adapted to conform to the three-dimensional feature thereby decorating the three-dimensional feature while generally maintaining the three-dimensional surface contours of the three-dimensional surface feature, wherein the cover is removable, and
   d) wherein the body further comprises an end cap that prevents the removal of the cover when applied to the body.

2. An oral care implement in accordance with claim 1, wherein the cover decoration is two-dimensional.

3. An oral care implement in accordance with claim 2, wherein the three-dimensional surface feature is undecorated.

4. An oral care implement in accordance with claim 3, wherein the oral care implement is a powered toothbrush.

5. An oral care implement in accordance with claim 4, further comprising cleaning elements on the head that are powered by a power element in the body.

6. An oral care implement in accordance with claim 5, wherein the cleaning elements are counter-oscillating.

7. An oral care implement in accordance with claim 1, wherein the three-dimensional surface feature is undecorated.

8. An oral care implement in accordance with claim 7, wherein the body further comprises a two-dimensional surface feature and wherein the cover includes a decoration that is associated with the two-dimensional surface feature such that the body also appears to have a decorated two-dimensional surface feature.

9. An oral care implement in accordance with claim 1, wherein the cover is non-adhesively attached to the body.

10. An oral care implement in accordance with claim 9, wherein the cover is attached by static cling.

11. An oral care implement in accordance with claim 1, wherein the three-dimensional surface feature further comprises a plurality of discontinuous surface contours.

12. An oral care implement in accordance with claim 11, wherein at least two surface contours are decorated differently by the application of the cover to the body.

* * * * *